United States Patent [19]

Karrer et al.

[11] Patent Number: 5,280,041
[45] Date of Patent: Jan. 18, 1994

[54] METHYLDIOXOLAN

[75] Inventors: Friedrich Karrer, Zofingen; Hans-Peter Buser; Gerardo Ramos, both of Arlesheim; Alfred Rindlisbacher, Muttenz; Luigi M. Venanzi, Zurich, all of Switzerland; Thomas R. Ward, Ithaca, N.Y.

[73] Assignee: Ciba-Geigy Corporation, Ardsley, N.Y.

[21] Appl. No.: 839,453

[22] Filed: Feb. 20, 1992

[30] Foreign Application Priority Data

Feb. 25, 1991 [CH] Switzerland .................. 572/91

[51] Int. Cl.⁵ .................. A01N 43/28; C07D 317/22
[52] U.S. Cl. .................. 514/467; 549/453
[58] Field of Search .................. 549/453; 514/467

[56] References Cited

U.S. PATENT DOCUMENTS 4,097,581 6/1978 Farooq et al. .

FOREIGN PATENT DOCUMENTS 2655910 6/1977 Fed. Rep. of Germany .

Primary Examiner—Nicky Chan
Attorney, Agent, or Firm—Marla J. Mathias; George R. Dohmann; Kevin T. Mansfield

[57] ABSTRACT

The novel 2R,4S-2-ethyl-4-[(4-phenoxyphenoxy)methyl]dioxolan of formula I

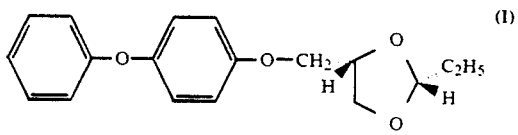

can be used as a pesticide. It is used to control especially insects in fruit and citrus crops.

4 Claims, No Drawings

METHYLDIOXOLAN

The present invention relates to the novel 2R,4S-2-ethyl-4-[(4-phenoxyphenoxy)methyl]-dioxolan, to processes for the preparation thereof, to pesticides comprising that compound, and to the use thereof in the control of pests of the division Arthropoda, especially of insects and representatives of the order Acarina. The invention relates also to novel intermediates which have been developed for the preparation of the novel compound.

The 2R,4S-2-ethyl-4-[(4-phenoxyphenoxy)methyl]dioxolan according to the invention corresponds to formula I

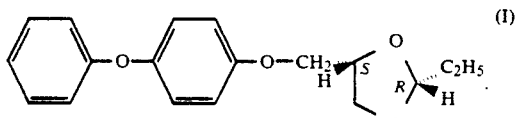

In the literature, the enantiomeric mixture of 2-ethyl-4-[(4-phenoxyphenoxy)methyl]dioxolan is known, for example, from DE-OS 2 655 910. The enantiomeric mixture is distinguished by the fact that it can be used successfully in the control of pests of the division Arthropoda, especially of the class Insecta and of the order Acarina. In spite of the good activity, the properties of the known isomeric mixture were not always completely satisfactory against all undesired pests when used as a pesticide. In particular, phytotoxic effects are occasionally observed in the treated crops of useful plants in unfavourable weather conditions and in the case of unintentional overdosing, for example when spray strips overlap as a result of wind drift or inaccurate strip spraying. There is therefore a continued need for a pest control composition having improved properties.

Surprisingly, this need can largely be satisfied by the use of the individual isomer of formula I proposed according to the invention, since it has been found that, as compared with the enantiomeric mixture, the 2R,4S-isomer according to the invention not only has improved, greater activity against the undesired pests, but also, surprisingly, is better tolerated by the treated plants than is the enantiomeric mixture. Increased activity and reduced phytotoxicity result in a wider safety margin for the user, which means that the amount of active ingredient applied may be increased if necessary, for example in order to control effectively even pests that are difficult to control, without the attendant risk of damage to the treated useful plants.

According to the invention, therefore, 2R,4S-2-ethyl-4-[(4-phenoxyphenoxy)methyl]dioxolan is proposed as a composition for pest control, especially for controlling insects and representatives of the order Acarina.

In principle, it is possible to obtain the compound of formula I according to the invention from the previously known enantiomeric mixture by separation methods suitable for enantiomers. Examples of such methods are physical methods, such as fractional crystallisation or chromatography, if desired also on chiral stationary phases, and also derivatisation with defined optically active auxiliary substances and separation of the resulting enantiomer pairs by the mentioned separation methods. The pure optical antipodes are then obtained from such isolated enantiomer derivatives by removal of the auxiliary substance. In practice, however, it is in most cases advantageous to prepare the desired individual isomer by specific stereoselective synthesis.

By means of such specific synthesis methods, the compound of formula I is obtained, for example, either by a) dehydrobrominating the bromoethyldioxolan of formula II

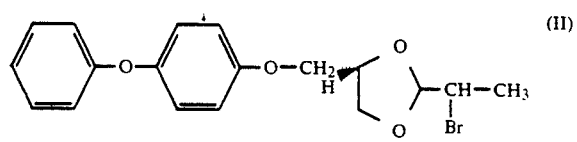

in the presence of tert-butanol and potassium tert-butoxide, and hydrogenating the resulting ketene acetal of formula III

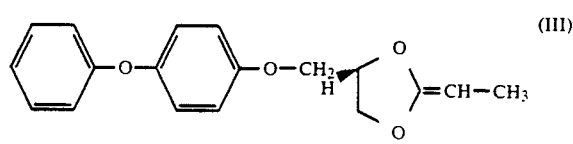

with hydrogen in the presence of a palladium/calcium carbonate catalyst, or b) reacting the diol of formula IV

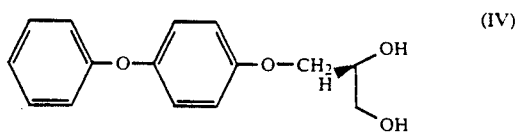

in the presence of the stereoselective catalyst of formula V

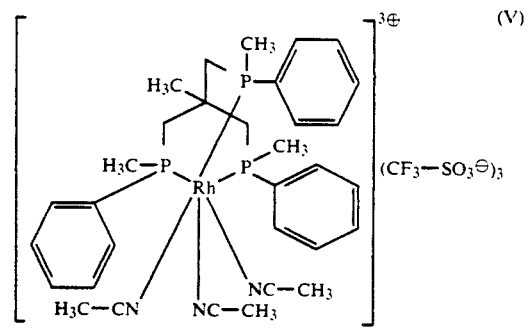

with a propionaldehyde acetal of formula VI

wherein R is $C_1$-$C_4$alkyl, preferably methyl or ethyl.

The above two processes are preferably carried out in suitable inert organic solvents. For process a) there are suitable especially alcohols, such as methanol, ethanol, isopropanol or, very especially, tert-butanol. For process b) there come into consideration aromatic hydrocarbons, such as toluene, xylene, mesitylene, benzene or Tetralin, or halogenated hydrocarbons, such as methylene chloride, chloroform, trichloroethane or tetrachloroethane. Process variants a) and b) yield the product of formula I with a very high optical purity. Enantiomers having undesired orientation of the substituents on the two asymmetric carbon atoms of the dioxolan ring are formed in only very small amounts. Typical degrees of isomeric purity are 94% in process a) and at least 90% in process b).

In a typical reaction, process a) is carried out in such a manner that the bromoethyldioxolan of formula II is suspended together with two equivalents of potassium tertbutoxide in dry tert-butanol and heated at a temperature of from $+80°$ C. to $+100°$ C. for approximately 4 hours. After cooling, this solution contains the ketene acetal of formula III. In order to avoid losses of that compound by hydrolysis and decomposition during the isolation, the resulting reaction product is reacted, without a further purification step, with hydrogen gas in an autoclave in the presence of a 2% to 15%, preferably 5%, palladium-on-calcium carbonate catalyst. Typical reaction conditions for this hydrogenation step are from 80 bar to 150 bar at temperatures of from $+15°$ C. to $+30°$ C. Working up yields the product of formula I in the 2R,4S-configuration with a purity of 94%. 6% of the resulting reaction product has the 2R,4R-configuration.

In its typical form, process b) is carried out in such a manner that the diol of formula IV and the propionaldehyde acetal of formula VI are introduced in equimolar amounts into a suitable solvent, and the catalyst of formula V is added in an amount of approximately from 0.01 to 0.0001, preferably 0.0005, molar equivalents. At a reaction temperature of from $+20°$ C. to $+30°$ C., the reaction times until the starting materials have reacted completely are up to 48 hours. Working up yields the product of formula I with a degree of purity of over 90% of the 2R,4-isomer. The proportion of the 2R,4R-isomer which is likewise formed is less than 10%.

The starting materials and intermediates of formulae II, III and IV have been developed specifically for the synthesis of the compound of formula I. The present invention therefore relates also to them. The intermediates of formula VI are known and are available commercially. The acetalisation catalyst of formula V is also novel and was developed specifically for synthesis process b).

The compound of formula II is obtained in an acetalisation reaction, by reacting the diol of formula IV in the presence of an acid catalyst with an α-bromopropionaldehyde acetal of formula VII

(VII)

wherein R is $C_1$-$C_4$alkyl, preferably methyl or ethyl.

The reaction (IV+VII→II) is carried out under the conditions customary for an acetalisation reaction. Preferably, an inert organic solvent is selected, such as an aromatic hydrocarbon, for example toluene or xylene, and the reactants are heated in equimolar amounts in the presence of an acid catalyst until the starting materials have reacted completely, at a temperature corresponding to the boiling point of the reaction mixture. Suitable acid catalysts are both strong inorganic acids, such as HCl, $H_2SO_4$ and $H_3PO_4$, and also organic acids, such as $F_3C$—COOH, $F_3C$—$SO_3$—H and $H_3C$—$C_6H_4$—$SO_3H$, and acid ion exchangers.

If desired, the intermediate of formula III may be isolated from the reaction mixture after the first process step of process variant a), by working up the reaction mixture after the elimination of HBr with the exclusion of water.

The diol of formula IV is advantageously obtainable by the following two processes.

According to a first process, the diol of formula IV is obtained by reacting 4-phenoxyphenol of formula VIII

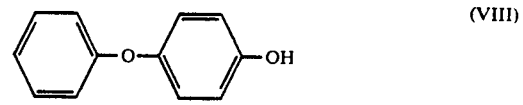

(VIII)

in the presence of a base, such as potassium tert-butoxide, in a polar solvent, such as dimethylsulfoxide, with 4R-2,2-dimethyl-4-tosyloxymethyldioxolan of formula IX

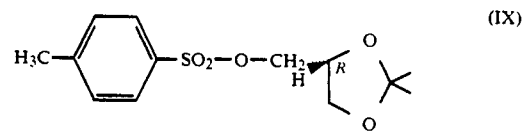

(IX)

and subjecting the resulting 4-phenoxyphenylmethyl ether of formula X

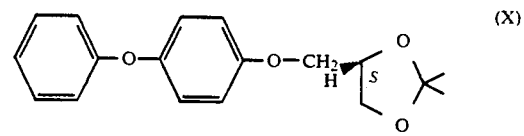

(X)

to hydrolysis in the presence of an acid catalyst.

The hydrolysis reaction (X→IV) is preferably carried out in a solvent, such as methanol, ethanol, isopropanol or water. The reaction temperatures in both reaction steps (VIII+IX→X and X→IV) are generally from $+10°$ C. to $+30°$ C. Inorganic and organic acids may be used as the acid catalyst. Examples are HCl, $H_2SO_4$, $H_3PO_4$, $CF_3SO_3H$ and $F_3C$—COOH. Acid ion exchangers may also be used as acid catalysts. Both reaction steps generally produce yields of from 90 to 95% of the theoretical yield. The optical purity of the product of formula IV is greater than 95%.

In a second process, the diol of formula IV is obtained by reacting racemic glycerol with a camphorsulfonamide of formula XI

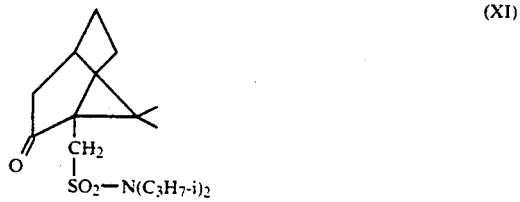

(XI)

in the presence of an acid catalyst, isolating from the resulting reaction mixture the crystallising individual diastereoisomer of formula XII

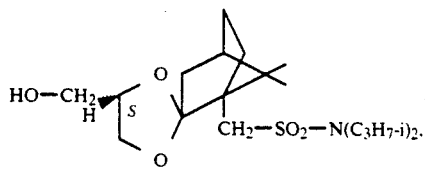

(XII)

converting the latter into the mesylate of formula XIII

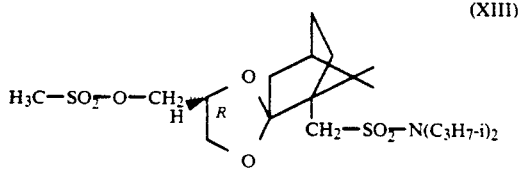

(XIII)

in the presence of a base, by means of methanesulfonic acid chloride, transetherifying the intermediate of formula XIII in the presence of a base with 4-phenoxyphenol of formula VIII, and hydrolysing the resulting adduct of formula XIV

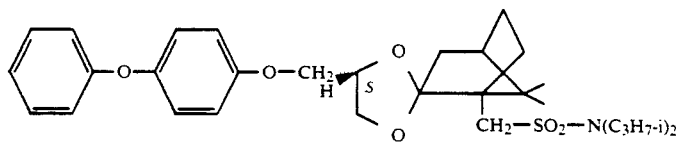

(XIV)

in the presence of an acid.

The first reaction step of this process for the preparation of the diol of formula IV is carried out under conditions customary for an acetalisation reaction (XI→XII). For example, this condensation step can be carried out in the presence of acids such as p-toluenesulfonic acid, camphor-10-sulfonic-acid or acid ion exchanger resin, in an anhydrous solvent, for example toluene or benzene, azeotropic distillation. The 4S individual diastereoisomer of formula XII can readily be separated from the mixture of the resulting acetals and identified on account of the fact that it crystallises from the diastereoisomeric mixture. It has a melting point of from 98° to 100° C. The third reaction step (XIII→XIV) takes place under the customary conditions of an $S_N$ reaction in the presence of a base. The use of potassium carbonate as the base has proved especially suitable in the present process step. In the fourth reaction step (XIV→IV), the hydrolysis of the acetal body is carried out under customary conditions in the presence of an acid, such as HCl, $H_2SO_4$ or $H_3PO_4$, in water or an aqueous reaction medium of methanol, ethanol or isopropanol. The diol of formula IV is obtained in this process variant with an optical purity of 98% and a melting point of 88.4° C. to 89.5° C. The optical rotation is $[\alpha]_D^{RT} = -6.34°$. In addition to the diol of formula IV, the camphorsulfonamide of formula XI is recovered in the last step of the reaction sequence, so that it can be used again when the reaction to prepare the compound IV is repeated.

The starting materials of formulae VII, VIII, IX and XI are known and are available commercially. The intermediates of formulae X and XIV are novel. They were developed specifically for the synthesis of the compound of formula I, and the present invention therefore relates also to them.

The novel stereoselective catalyst of formula V was likewise developed specifically for the synthesis of the compound of formula I. That stereoselective acetalisation catalyst is obtained by reacting 3 equivalents of methylphenylphosphine lithium of formula XV

(XV)

with trichloroneopentane of formula XVI

$H_3C—C(CH_2Cl)_3$     (XVI).

converting the resulting triphosphine of formula XVII

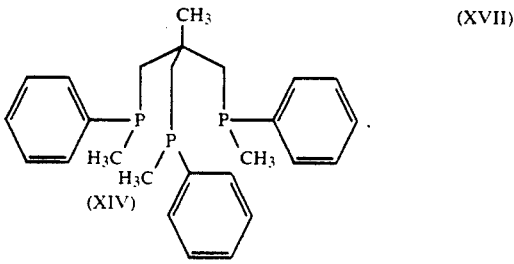

(XVII)

by means of bicyclo[2.2.1]hepta-2,5-diene rhodium(I) chloride dimer of formula XVIII

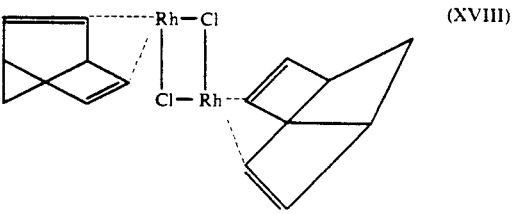

(XVIII)

and silver trifluoromethanesulfonate ($F_3C—SO_2—O—Ag$), into a complex of formula XIX

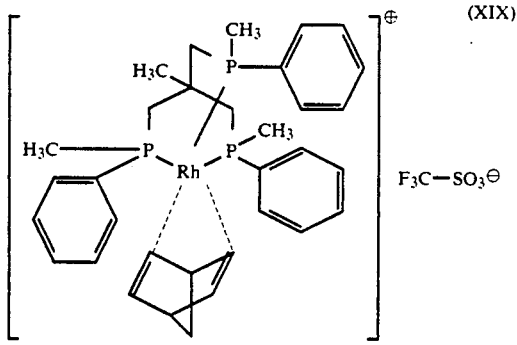

and treating that pre-product in acetonitrile with trifluoromethanesulfonic acid.

The starting materials of formulae XV, XVI and XVIII for the preparation of the catalyst V are known in the literature. The intermediates of formulae XVII and XIX are novel and were developed specifically for the synthesis of the novel catalyst of formula V.

It has now been found that the compound of formula I according to the invention is a valuable active ingredient in pest control while being well tolerated by warm-blooded animals, fish and plants. The compound according to the invention can be used especially against insects and arachnids which occur on useful plants and ornamentals in agriculture, especially in cotton, vegetable and fruit crops, in forestry, in the protection of stored goods and material stocks, and also in the hygiene sector, especially on domestic animals and productive livestock. It is effective against all or individual development stages of normally sensitive and also resistant species. Its action may manifest itself in the death of the pests immediately or only at a later date, for example at moulting, or in reduced oviposition and/or a reduced hatching rate. The above-mentioned pests include:

of the order Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

of the order Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

of the order Orthoptera, for example Blatta spp., Blattella spp., Gryllotalpa spp., *Leucophaea maderae*, Locusta spp., Periplaneta spp. and Schistocerca spp.;

of the order Isoptera, for example Reticulitermes spp.;

of the order Psocoptera, for example Liposcelis spp.;

of the order Anoplura, for example Haematopinus spp., Linognathus spp., Pediculus spp., Pemphigus spp. and Phylloxera spp.;

of the order Mallophaga, for example Damalinea spp. and Trichodectes spp.;

of the order Thysanoptera, for example Frankliniella spp., Hercinothrips spp., Taeniothrips spp., *Thrips palmi, Thrips tabaci* and *Scirtothrips aurantii;* of the order Heteroptera, for example Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

of the order Homoptera, for example *Aleurothrixus floccosus, Aleyrodes brassicae*, Aonidiella spp., Aphididae, Aphis spp., Aspidiotus spp., Bemisia tabaci, Ceroplaster spp., *Chrysomphalus aonidium, Chrysomphalus dictyosperimi, Coccus hesperidum*, Empoasca spp., Eriosoma larigerum, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum*, Trioza erytreae and Unaspis citri;

of the order Hymenoptera, for example Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

of the order Diptera, for example Aedes spp., *Antherigona soccata*, Bibio hortulanus, *Calliphora erythrocephala*, Ceratitis spp., Chrysomya spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.;

of the order Siphonaptera, for example Ceratophyllus spp., Xenopsylla cheopis;

of the order Acarina, for example *Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.; and of the order Thysanura, for example *Lepisma saccharina*.

The compound of formula I is suitable especially for controlling pests in fruit and citrus crops. In particular, scale-insects, such as *Aonidiella aurantii, Saissetia olea*,

*Lepidosaphes beckii, Quadraspidiotus perniciousus, Planococcus citri, Unaspis citri, Ceroplastes floridensis, Ceroplastes sinensis, Parlatoria pergandei* and *Lepidosaphes ulmi*, and fruit pests, such as *Adoxophyes orana, Cydia pomonella, Psylla piricola Leucoptera scitella* and *Lobesia botrana*, are controlled effectively. Good activity is also observed against the rice pest *Nilaparvata lugens* and against ticks, such as *Boophilus microplus*.

The good pesticidal activity of the compound of formula I according to the invention corresponds to a mortality of at least 50–60% of the mentioned pests.

The activity of the compound of the invention and of the compositions comprising it can be substantially broadened and adapted to prevailing circumstances by the addition of other insecticides and/or acaricides. Examples of suitable additives include representatives of the following classes of compounds: organophosphorus compounds, nitrophenols and derivatives thereof, formamidines, ureas, carbamates, pyrethroids, chlorinated hydrocarbons, and Bacillus thuringiensis preparations.

The compound of formula I us used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the nature of the compositions, the methods of application, such as spraying, atomising, dusting, scattering or pouring, are chosen in accordance with the intended objectives and the prevailing circumstances. The compound of formula I is also suitable for use in the treatment of seeds. It is possible both to treat or dress the seeds with the active ingredient or with a formulation comprising the active ingredient before sowing, and to apply the active ingredient to the furrow at the time of sowing.

The formulations, i.e. the compositions, preparations or mixtures comprising the compound (active ingredient) of formula I, or combinations of that compound with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the $C_8$ to $C_{12}$ fractions of alkylbenzenes such as xylene mixtures or alkylated naphthalenes, aliphatic or cycloaliphatic hydrocarbons such as cyclohexane, paraffins or tetrahydronaphthalene, alcohols such as ethanol, propanol or butanol, and glycols and their ethers and esters such as propylene glycol, dipropylene glycol ether, ethylene glycol, ethylene glycol monomethyl or monoethyl ether, ketones such as cyclohexanone, isophorone or diacetone alcohol, strongly polar solvents such as N-methyl-2-pyrrolidone, dimethyl sulfoxide or dimethylformamide, or water, vegetable oils such as rape oil, castor oil, coconut oil or soybean oil; and, where appropriate, also silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, e.g. especially dolomite or pulverised plant residues.

Depending on the nature of the compound of formula I to be formulated, or of the combinations of that compound with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants. Cationic surfactants are preferably quaternary ammonium salts which contain, as N-substituent, at least one $C_8-C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, N.J., USA, 1988, H. Stache, "Tensid-Taschenbuch", 2nd edition, C. Hanser Verlag, Munich, Vienna 1981, M. and J. Ash, "Encyclopedia of Surfactants", Vol. I-III, Chemical Publishing Co., New York, 1980-1981.

The pesticidal compositions usually comprise 0.1 to 99%, preferably 0.1 to 95%, of a compound of formula I or combinations of that compound with other insecticides or acaricides, 1 to 99.9% of a solid or liquid adjuvant, and 0 to 25%, of a surfactant. Whereas commercial products will preferably be formulated as concentrates, the end user will normally employ dilute formulations which have considerably lower active ingredient concentrations. Typical application concentrations are from 0.1 to 1000 ppm, preferably from 0.1 to 500 ppm. The rates of application per hectare are generally from 1 to 1000 g of active ingredient per hectare, preferably from 25 to 500 g/ha.

Preferred formulations have especially the following composition (throughout, percentages are by weight):

| Emulsifiable concentrates: | |
| --- | --- |
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further auxiliaries such as stabilisers, for example vegetable oils or epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

The following Examples serve to illustrate the invention, but do not limit the invention.

EXAMPLE P1

2R,4S-2-Ethyl-4-[(4-phenoxyphenoxy)methyl]dioxolan

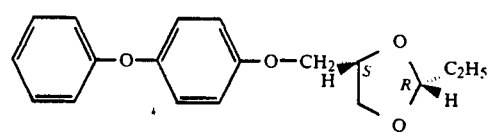

a) 2RS,4S-2-(1-bromoethyl)-4-[(4-phenoxyphenoxy)methyl]dioxolan

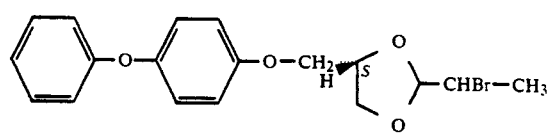

167 g of 2R-2,3-dihydroxy-1-(4-phenoxyphenoxy)-propane, 162.5 g of 2-bromopropionaldehydediethyl acetal and 167 g of acidic ion exchanger resin (DOWEX 50W.8, 16-40 mesh, H⊕ form) are mixed with 1.3 liters of toluene and heated under reflux for 5.5 hours. During that time, 700 ml of an azeotrope of and toluene are distilled off from the mixture. After cooling to room temperature, the ion exchanger resin is filtered off and the filtrate is concentrated by evaporation. The residue is chromatographed over 1.2 kg of silica gel using an eluant mixture of hexane/ethyl acetate (5:1). 223.3 g of 2RS,4S-2-(1-bromoethyl)-4-[(4-phenoxyphenoxy)methyl]dioxolan are obtained in the form of a slightly yellowish oil, $n_D^{20}$:1.5691.

b) 4S-2-Ethylidene-4-[(4-phenoxyphenoxy)methyl]dioxolan

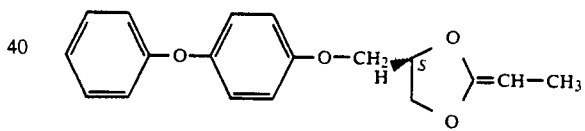

A suspension of 50 g of 2RS,4S-2-(1-bromoethyl)-4-[(4-phenoxyphenoxy)methyl]-dioxolan, 29.65 g of freshly sublimed potassium tert-butoxide and 500 ml of tert-butanol freshly distilled over CaO is stirred at a temperature of +95° C. for 3.5 hours under an argon atmosphere. After cooling to +25° C., that mixture is used directly in the following reaction step.

c) The reaction mixture obtained under Example P1 b) is rinsed with a further 300 ml of tert-butanol in an autoclave, with air-tight sealing. After the addition of 31.4 g of 5% dried palladium-on-calcium carbonate catalyst, hydrogen gas is introduced under pressure up to a pressure of 120 bar. The reactor is kept at +30° C. for 38 hours. The reaction mixture is then diluted with 150 ml of ethanol and filtered over diatomaceous earth. The filtrate is concentrated by evaporation, taken up in ethyl acetate, washed with water, dried over sodium sulfate and concentrated by evaporation. The resulting 38.3 g of crude product are purified by chromatography over 500 g of silica gel using a hexane/diethyl ether mixture (9:1) as eluant, yielding 22.8 of the product having an optical purity of 94% of the 2R,4S-enantiomer, and a further fraction of 8.55 g of the product having a purity of less than 90%.

EXAMPLE P2

2R-2,3-Dihydroxy-1-(4-phenoxyphenoxy)propane

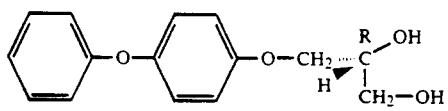

a) 4S-2-Spiro[(10-diisopropylaminosulfonyl)-2-bornane]-4-hydroxymethyldioxolan

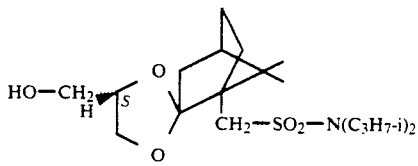

4.8 g of 10-diisopropylaminosulfonylcamphor, 1.6 ml of glycerol and 230 mg of p-toluenesulfonic acid monohydrate are taken up in 90 ml of benzene. The suspension is boiled for 37 hours using a water separator. If a thin-layer chromatogram indicates an incomplete reaction, a further 1.6 ml of glycerol and 234 mg of p-toluenesulfonic acid are added, and the mixture is boiled for a further 23 hours using the water separator.

Concentration of the reaction mixture by evaporation and chromatography of the residue over silica gel using a hexane/ethyl acetate mixture (4:1) yield, in addition to 1.63 g of a diastereoisomeric mixture, 1.45 g of the diastereoisomerically pure 4S-2-spiro[(10-diisopropylaminosulfonyl)-2-bornane]-4-hydroxymethyldioxolan in crystalline form with a melting point of 98°-100° C. The absolute configuration of the spiro-carbon atom was not determined.

b) 4R-2-Spiro[(10-diisopropylaminosulfonyl)-2-bornane]-4-methylsulfonyloxymethyldioxolan

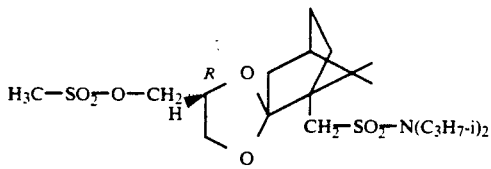

To a solution of 482.5 mg of 4S-2-spiro[(10-diisopropylaminosulfonyl)-2-bornane]-4-hydroxymethyldioxolan in 10 ml of methylene chloride there are added at 0° C. first 270 μl of triethylamine and then 120 μl (1.54 mmol) of methanesulfonyl chloride. After stirring at room temperature for 5 hours, the slightly yellowish reaction solution is poured onto 20 ml of 1N aqueous hydrochloric acid and diluted with 40 ml of methylene chloride. The organic phase is extracted twice with 20 ml of 1N hydrochloric acid each time. All the aqueous phases are washed with 2×50 ml of methylene chloride. The combined organic phases are dried over sodium sulfate and concentrated. Drying in vacuo yields 580 mg of diastereoisomerically pure 4R-2-spiro[(10-diisopropylaminosulfonyl)-2-bornane]-4-methylsulfonyloxymethyldioxolan in the form of a colourless oil which crystallises when left to stand; m.p. 60.5°-63.5° C.

c) 4S-2-Spiro[(10-diisopropylaminosulfonyl)-2-bornane]-4-(4-phenoxyphenoxymethyl)dioxolan

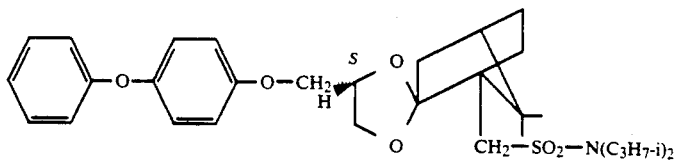

1.5 g of 4R-2-spiro[(10-diisopropylaminosulfonyl)-2-bornane]methylsulfonyloxymethyldioxolan, 720 mg of 4-phenoxyphenol and 970 mg of anhydrous potassium carbonate are taken up in 10 ml of dimethyl sulfoxide, and the mixture is then stirred at 100° C. for 20 hours. The reaction mixture is then poured onto water and extracted three times with ether. The ethereal phases are washed with water and brine, combined, dried over magnesium sulfate and concentrated. Chromatography of the oily residue over silica gel using a hexane/ethyl acetate mixture (8:1) yields 1.44 g of 4S-2-spiro[(10-diisopropylaminosulfonyl)-2-bornane]-4-(4-phenoxyphenoxymethyl)dioxolan in the form of a colourless oil.

d) 2.04 g of 4S-2-spiro[(10-diisopropylaminosulfonyl)-2-bornane]-4-(4-phenoxyphenoxymethyl)dioxolan are dissolved in 25 ml of methanol, and 10 ml of 4N aqueous hydrochloric acid are added at room temperature. The suspension, which immediately turns milky, is stirred at +50° C. for 16 hours. Then the reaction mixture is diluted with a 9:1 mixture of methanol and water and extracted three times with cyclohexane. The cyclohexane phases are washed twice with 75 ml of a 9:1 mixture of methanol and water, combined, dried over magnesium sulfate and concentrated. 920 mg of a colourless oil are obtained as residue. The methanol/water phases are combined and concentrated completely by evaporation. The residue is taken up in water and extracted three times with ether. The ethereal phases are washed with brine, combined, dried over magnesium sulfate and concentrated. In this manner, a further 2.1 g of colourless oil are obtained as residue. The two oily residues are combined (total 3.02 g) and stirred into boiling hexane. With vigorous stirring, the mixture is then slowly cooled to 0° C. and the crystallisate that forms is filtered off. Drying in vacuo yields 797 mg of optically pure (more than 98% ee) (−)-rotatory 2R-2,3-dihydroxy-1-(4-phenoxyphenoxy)propane, m.p. 88.4°-89.5° C., $[\alpha]_{589}{}^N = -6.34°$ By concentrating the mother liquor completely by evaporation, 1.08 g of the 10-diisopropylaminosulfonylcamphor that was used are recovered in the form of an oil.

EXAMPLE P3

2R,4S-2-Ethyl-4-[(4-phenoxyphenoxy)methyl]dioxolan a) α,α',α"-tris(methylphenylphosphino)neopentane

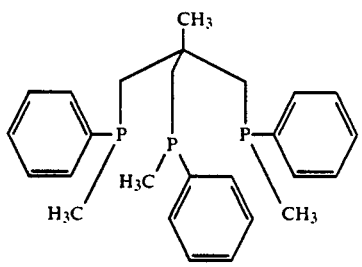

400 ml of a solution of 12 g of methylphenylphosphine in degassed tetrahydrofuran are cooled to −78° C. in a one-liter three-necked flask. 66.2 ml of butyllithium are added dropwise within a period of 20 minutes, and the mixture is stirred at −78° C. for one hour. After warming to room temperature, 5.62 g (0.032 mol) of α,α',α"-trichloroneopentane are added dropwise within a period of 35 minutes. The mixture is then heated under reflux for 2 hours. 250 ml of degassed ether and 50 ml of degassed water are added to the solution, and the organic phase is separated off and dried over magnesium sulfate. Removal of the solvent by evaporation using a water-jet vacuum yields 12.14 g of α,α',α"-tris(methylphenylphosphino)neopentane as crude product in the form of a light-yellow oil.

Purification is effected by stirring the crude product, under reflux, with 250–300 ml of degassed methanol until the solution becomes clear light-yellow. It is cooled to −78° C. and the methanol solution is drawn off from the frozen oil, yielding the analytically pure product in the form of a clear oil, yield 8.77 g.

Elemental analysis calculated for $C_{26}H_{33}P_3$(438.47): C: 71.22; H:7.59; P:21.19, found C: 71.28; H:7.58; P:21.45.

1H-NMR (200 MHz,CDCl$_3$): 7.59–7.26 (m,Ph), 2.30–1.78 (m, 2J (P,H)=3.7 Hz, PCH$_2$). 1.34–1.23 (3xd,2 (P,H)=3,7 Hz, PCH$_3$, RRS/SSR, RSR/SRS, SRR/RSS) 1.16 (d, 2J(P,H)=3.7 Hz, PCH$_3$, RRR/SSS), 1.03 (s, CH$_3$, RRR/SSS), 1.01 (s, CH$_3$, RRS/SSR, RSR/SRS, RSS/SRR).

31P-NMR (200 MHz, CDCl$_3$): −44.89 (S, RRR/SSS), −45.08 (s, RRS/SSR, RSR/SRS, RSS/SRR).

13C-NMR (200 MHz, CDCl$_3$): 141.6 (d, 1J(P,C)=11.9 Hz, PC1) 132.3 (d, 2J (P,C)=19.9 Hz, PC2), 128.5 (d, 3J (P,C)=6 Hz,PC3), 128.3 (s, PC4), 46.0 (d.t, 1J (P,C)=14 Hz, 4J (P,C)=8 Hz, PCH$_2$), 38.4 (q, 3J (P,C)=12.6 Hz, CH$_3$),29.1 (d, 2J P,C)=9 Hz, C), 14.6 d, 1J (P,C)=12 Hz, PCH$_3$).

b) α,α',α"-Tris(methylphenylphosphino)-neopentane--norbonanediene-rhodium(I)trifluoromethanesulfonate complex

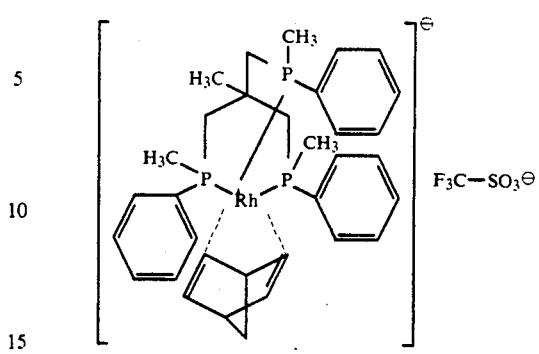

990 mg of α,α',α"-tris(methylphenylphosphino)neopentane in 20 ml of degassed acetone are introduced into a 250 ml two-necked flask and cooled to −78° C. 521 mg of dimeric rhodium(I)-norbonadiene-chloro complex and 581 mg of silver trifluoromethanesulfonate (Ag—O—SO$_2$—CF$_3$) are dissolved in 100 ml of degassed acetone, and the mixture is stirred for 20 minutes. At −78° C., the latter solution is added to the phosphine solution over a paper filter. The mixture is warmed to room temperature and the solvent is removed by evaporation. The crude yield of the resulting α,α',α"-tris(methylphenylphosphino)-neopentane-norbonadiene-rhodium(I)-trifluoromethanesulfonate complex in the form of a deep yellow powder is 1.74 g.

Recrystallisation is effected by dissolving the crude product in 23 ml of acetone and adding 18 ml of ether, which is added to the stirred solution carefully over a period of 15 minutes. After a further 15 minutes, the solution becomes slightly cloudy and, for the purpose of crystallisation, is cooled to 0° C. for 18 hours. The resulting orange powder is filtered off and washed with pentane. Yield: 360 mg of analytically pure product.

The mother liquor is concentrated to about 20 ml of acetone, and then pentane is added until precipitation occurs; the precipitate is filtered off and washed with pentane. In this manner, a further 1.06 g of product are obtained.

Elemental analysis calculated for $C_{34}H_{41}O_3F_3P_3SRh$ (782.58); C: 52.18 H: 5.28. found C: 51.68 H: 5.32.

31P-NMR (101 MHz, CDCl$_3$): 14.2 (d.t,1J(Rh,P)=112 Hz 2J(P,P)=46 Hz), -3.7 (d.d.d,1J(Rh,P)=113 Hz, 2J(PS,PR)=46 Hz, 2J(PS,PR)=31 Hz),

1H-NMR (200 MHz,CDCl$_3$): 8.2–6.6(m,Ph), 3.7 (m,=CH), 3.4(m,CH), 3.1(m,CH$_2$), 2.5–2.0(3xd,1J(P,H)=14 Hz,P-CH$_3$), 1.8–1.0(m,1J(H,H)=7 Hz 2J(Rh,H)=140 Hz,P-CH$_2$), 1.9–1.7(g,4J(P,H)=10 Hz,PCH$_3$).

IR (RbI-Pressing): 3054 (m), 2987 (m), 2919 (m), 1433 (m); 1272 (s), 1221 (m), 1148 (s), 1097 (m); 1029 (s), 899 (s), 880 (s), 741 (m); 696 (m), 636 (m), 492 (m), 460 (m), c) α,α',α"-Tris(methylphenylphosphino)-neopentane-tris(acetonitrile)-rhodium(III)-tris-trifluoromethanesulfonate complex

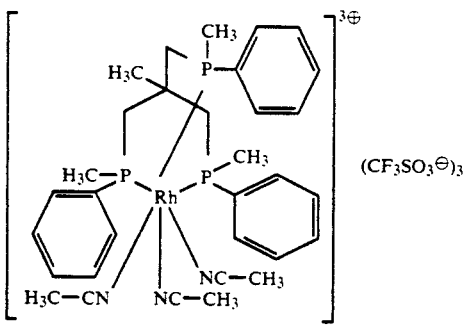

100 mg of the complex obtained according to Example P3c) are dissolved in 2 ml of degassed acetonitrile in a 10 ml flask, and the solution is saturated with hydrogen gas for 10 minutes. 126 μl of trifluoromethanesulfonic acid are added by means of a micro-syringe, whereupon the orange solution turns yellow. After stirring for 15 minutes, the α,α′,α″-tris(methylphenylphosphino)-neopentane-tris(acetonitrile)-rhodium(III)-tris-trifluoromethanesulfonate complex is precipitated from the solution by means of degassed ether. The white precipitate is removed by centrifugation and washed with ether and pentane. Yield: 132 mg of analytically pure catalyst of formula V.

Elemental analysis calculated for $C_{35}H_{42}N_3O_9F_9P_3S_3Rh$ (1111.73): C: 37.81 H: 3.81 N: 3.78. found C: 35.85 H: 3.72 N: 2.69.

d) 26 g of 2RS-2,3-dihydroxy-1-(4-phenoxyphenoxy)-propane and 14.5 g of propionaldehydediethyl acetal are dissolved in 30 ml of toluene. 55 mg of the acetalisation catalyst prepared according to Example 3Pc) are added to that mixture, which is stirred at room temperature for 50 hours, yielding 29 g of pure 2R,4S-2-ethyl-4-[(4-phenoxyphenoxy)methyl]dioxolan having an optical purity greater than 90%, in the form of a colourless oily liquid having a refractive index of $n_D^{20}$: 1.5459.

EXAMPLE P4

2R-2,3-Dihydroxy-1-(4-phenoxyphenoxy)propane a) 4S-2,2-Dimethyl-4-[(4-phenoxyphenoxy)methyl]-dioxolan

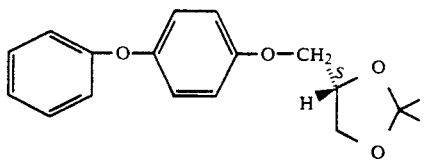

A total of 25.3 g of potassium tert-butoxide are added in portions at room temperature, with stirring and under a nitrogen atmosphere, and with slight external cooling, to a solution of 38.1 g of 4-phenoxyphenol in 350 ml of anhydrous dimethylsulfoxide. Then, within a period of one hour and at room temperature, a solution of 64.4 g of D-α,β-isopropylideneglycerol γ-tosylate in 30 ml of dimethylsulfoxide is added dropwise to the resulting green solution. The mixture is stirred at room temperature for 65 hours and is then poured onto 500 ml of ice-water and extracted repeatedly with diethyl ether. The combined ethereal phases are washed repeatedly with water and saturated sodium chloride solution, dried over sodium sulfate, and the ether is removed by distillation, yielding 4S-2,2-dimethyl-4-[(4-phenoxyphenoxy)methyl]-1,3-dioxolan in the form of a light-yellow oil which solidifies in crystalline form after some time, $[\alpha]_D^{20} = +5.5°$ (CHCl$_3$)/purity ee ~99%, m.p. 36.5°–37° C.

b) 60 g of acidic ion exchange resin (DOWEX 50 W 8 H$^{\oplus}$ form, 16–40 mesh) are added to a solution of 63.9 g of 4S-2,2-dimethyl-4-[(4-phenoxyphenoxy)methyl]-1,3-dioxolan in 500 ml of pure methanol, and the mixture is stirred vigorously at room temperature for 48 hours. The methanol solution is then filtered off from the ion exchanger, the exchange resin is washed repeatedly with methanol, and the solvent is removed from the combined methanol solutions by distillation in vacuo. The crude product is dissolved in 150 ml of ethyl acetate with the application of heat, filtered while hot through a glass suction filter, a total of 125 ml of n-hexane are added, and the mixture is made to crystallise by cooling. The resulting colourless crystals of 2R-2,3-dihydroxy-1-(4-phenoxyphenoxy)propane have a melting point of 88.6°–89.5° C., purity: ee ~99%, $[\alpha]_D^{20}$: −6.7°±0.8° (ethanol).

FORMULATION EXAMPLES (THROUGHOUT, PERCENTAGES ARE BY WEIGHT)

| Example F1: Wettable powders | a) | b) | c) |
| --- | --- | --- | --- |
| compound 1 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient or active ingredient combination is mixed with the adjuvants and the mixture is thoroughly ground in a suitable mill, affording wettable powders which can be diluted with water to give suspensions of the desired concentration.

| Example F2: Emulsifiable concentrate | |
| --- | --- |
| compound 1 | 10% |
| octylphenol polyethylene glycol ether (4-5 mol of ethylene oxide) | 3% |
| calcium dodecylbenzenesulfonate | 3% |
| castor oil polyethylene glycol ether (36 mol of ethylene oxide) | 4% |
| cyclohexanone | 30% |
| xylene mixture | 50% |

Emulsions of any desired concentration can be produced from this concentrate by dilution with water.

| Example F3: Dusts | a) | b) |
| --- | --- | --- |
| compound 1 | 5% | 8% |
| talcum | 95% | — |
| kaolin | — | 92% |

Ready-for-use dusts are obtained by mixing the carrier with the active ingredient and grinding the mixture in a suitable mill.

| Example F4: Extruder granules | |
| --- | --- |
| compound 1 | 10% |

-continued

| Example F4: Extruder granules | |
|---|---|
| sodium lignosulfonate | 2% |
| carboxymethylcellulose | 1% |
| kaolin | 87% |

The active ingredient or active ingredient combination is mixed and ground with the adjuvants, and the mixture is moistened with water. The mixture is extruded, granulated and then dried in a stream of air.

| Example F5: Coated granules | |
|---|---|
| compound I | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granules are obtained in this manner.

| Example F6: Suspension concentrate | |
|---|---|
| compound I | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient or active ingredient combination is intimately mixed with the adjuvants, giving a suspension concentrate from which suspensions of any desired concentration can be obtained by dilution with water.

BIOLOGICAL EXAMPLES

EXAMPLE B1

Action against *Nilaparvata lugens*

Rice plants are sprayed with an aqueous emulsion comprising 400 ppm of the compound of formula I. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

The compound of formula I exhibits good activity against Nilaparvata lugens in this test.

EXAMPLE B2

Action against *Boophilus microplus*

Adult female ticks which are replete with blood are affixed to a PVC plate and covered with a cotton wool swab. For treatment, 10 ml of an aqueous test solution comprising 125 ppm of the compound of formula I are poured over the test insects. The cotton wool swab is then removed and the ticks are incubated for 4 weeks until oviposition has taken place. The action against Boophilus microplus manifests itself either as morality or sterility in the females, or as ovidical action in the eggs.

The compound of formula I exhibits good activity against *Boophilus microplus* in this test.

EXAMPLE B3

Ovicidal action against *Adoxophyes reticulana*

Egg deposits of *Adoxophyes reticulana* on filter paper are immersed for a short time in an aqueous acetone test solution comprising 400 ppm of the compound of formula I. After the test solution has dried, the eggs are incubated in petri dishes. After 6 days, the percentage of eggs which have hatched is evaluated in comparison with untreated controls (% reduction in hatching rate).

The compound of formula I exhibits good activity against *Adoxophyes reticulana* in this test.

EXAMPLE B4

Ovicidal action against *Lobesia botrana*

Egg deposits of *Lobesia botrana* on filter paper are immersed for a short time in an aqueous acetone test solution comprising 400 ppm of the compound of formula I. After the test solution has dried, the eggs are incubated in petri dishes. After 6 days, the percentage of eggs which have hatched is evaluated in comparison with untreated controls (% reduction in hatching rate).

The compound of formula I exhibits good activity against *Lobesia botrana* in this test.

EXAMPLE B5

Action against *Aonidiella aurantii*

Potato tubers are populated with crawlers of *Aonidiella aurantii* (red citrus scale). After about 2 weeks, the potatoes are immersed in an aqueous emulsion or suspension comprising the test compound in a concentration of 400 ppm. After the treated potato tubers have dried, they are incubated in a plastics container. Evaluation is made 10–12 weeks later by comparing the survival rate of the crawlers of the first subsequent generation of the treated scale population with that of untreated controls.

The compound of formula I exhibits good activity against *Aonidiella aurantii* in this test. In particular, the compound of formula I remains 100% effective at a concentration of 0.1 ppm, whereas with the previously known enantiomeric mixture having the same structure, such complete activity was achieved only at 0.75 ppm.

EXAMPLE B6

Ovicidal action against *Heliothis virescens*

Egg deposits of *Heliothis virescens* on filter paper are immersed for a short time in an aqueous acetone test solution comprising 400 ppm of the compound of formula I. After the test solution has dried, the eggs are incubated in petri dishes. After 6 days, the percentage of eggs which have hatched is evaluated in comparison with untreated controls (% reduction in hatching rate).

The compound of formula I exhibits good activity against *Heliothis virescens* in this test. In particular, this compound exhibits 90% activity at only 200 ppm, whereas the previously known enantiomeric mixture is ineffective at 400 ppm.

EXAMPLE B7

Phytotoxicity test

Cotton plants in the 4-leaf stage are sprayed with aqueous suspensions of the test compounds in concentrations of 2000, 1000, 500 and 250 ppm. After the spray coating has dried, the treated plants are cultivated in a greenhouse. After 7 days, the test is evaluated by assessing the damage in percent to the treated plants in comparison with that to untreated control plants.

| | Result: Test plant cotton Evaluation 7 days after application | |
|---|---|---|
| | Phytotoxicity in % | |
| Concentration ppm | Compound of formula I | Previously known enantiomeric mixture of the same structure |
| 2000 | 15 | 25 |
| 1000 | 5 | 15 |
| 500 | <2.5 | 5 |
| 250 | <2.5 | 0 |

In this test, the compound of formula I exhibits markedly reduced damage to the treated cultivated plants as compared with the previously known enantiomeric mixture. The same degrees of damage were obtained with the previously known enantiomeric mixture at half the active ingredient concentration of the individual isomer of formula I according to the invention.

What is claimed is:
1. The compound 2R,4S-2-ethyl-4-[(4-phenoxyphenoxy)methyl]dioxolan of formula I

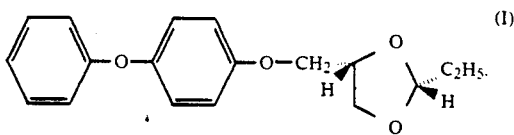

2. A method of controlling phytopathogenic pests, which comprises treating the pests or their locus with an effective amount of the compound of formula I according to claim 1.

3. A pesticidal composition comprising as active ingredient the compound of formula I according to claim 1 and at least one carrier.

4. A method of controlling insects and representatives of the order Acarina that are harmful to animals and plants, which comprises treating the pests or their locus with an effective amount of the compound of formula I according to claim 1.

* * * * *